United States Patent
Kondo et al.

(10) Patent No.: US 8,643,440 B2
(45) Date of Patent: Feb. 4, 2014

(54) ELECTRIC CIRCUIT, SENSOR SYSTEM EQUIPPED WITH THE ELECTRIC CIRCUIT, AND SENSOR DEVICE EQUIPPED WITH THE ELECTRIC CIRCUIT

(75) Inventors: Takayuki Kondo, Chino (JP); Masayoshi Todorokihara, Munich (DE); Yoshihiko Nimura, Suwa-gun (JP); Takeo Kawase, Suwa (JP)

(73) Assignee: Seiko Epson Corporation, Tokyo (JP)

(*) Notice: Subject to any disclaimer, the term of this patent is extended or adjusted under 35 U.S.C. 154(b) by 0 days.

(21) Appl. No.: 12/835,108

(22) Filed: Jul. 13, 2010

(65) Prior Publication Data

US 2011/0050352 A1    Mar. 3, 2011

(30) Foreign Application Priority Data

Aug. 27, 2009  (JP) ................. 2009-196512

(51) Int. Cl.
*H03K 3/03*     (2006.01)

(52) U.S. Cl.
USPC ................... 331/46; 331/44; 377/19; 377/44; 377/106

(58) Field of Classification Search
USPC ......... 331/44, 46; 327/76.48; 377/19, 44, 106
See application file for complete search history.

(56) References Cited

U.S. PATENT DOCUMENTS

| | | | |
|---|---|---|---|
| 2,627,033 A | 1/1953 | Jensen et al. | |
| 2,840,812 A | 6/1958 | Di Giacomo | |
| 2,944,219 A | 7/1960 | Tanaka et al. | |
| 3,026,473 A | 3/1962 | De Mott | |
| 3,056,085 A | 9/1962 | James et al. | |
| 3,144,623 A | 8/1964 | Steiner | |
| 3,227,952 A | 1/1966 | Proebster et al. | |
| 3,310,660 A | 3/1967 | Cogar | |
| 3,372,346 A | 3/1968 | Rogers et al. | |
| 3,407,290 A | 10/1968 | Atrubin | |
| 3,440,617 A | 4/1969 | Lesti | |
| 3,486,007 A | 12/1969 | Jacobson | |
| 3,551,826 A | 12/1970 | Sepe | |
| 3,553,579 A | 1/1971 | Teixeira | |

(Continued)

FOREIGN PATENT DOCUMENTS

| JP | 53-111768 | 9/1978 |
|---|---|---|
| JP | A-56-169923 | 12/1981 |

(Continued)

OTHER PUBLICATIONS

Katano, K., "Introduction to Proper Method for Using Measuring Insruments; How to Use Timing Devices," Transistor Technology Seminar, 14th Installment, Feb. 1994, p. 331-338 (with English translation).

(Continued)

*Primary Examiner* — Arnold Kinkead
*Assistant Examiner* — Richard Tan
(74) *Attorney, Agent, or Firm* — Oliff & Berridge, PLC (57) ABSTRACT

An electric circuit includes: a reference signal generation circuit that generates a reference signal based on a first oscillation signal that is an oscillation signal of a first oscillation circuit that vibrates a first vibrator; and a counter circuit that counts a second oscillation signal that is an oscillation signal of a second oscillation circuit that vibrates a second vibrator based on the reference signal, and outputs a count signal, wherein the count signal is a change of the count value in the second oscillation signal.

12 Claims, 5 Drawing Sheets

(56) References Cited

U.S. PATENT DOCUMENTS

| | | |
|---|---|---|
| 3,557,796 A | 1/1971 | Keller et al. |
| 3,605,017 A | 9/1971 | Chertok et al. |
| 3,609,308 A | 9/1971 | Lemon et al. |
| 3,624,494 A | 11/1971 | Turan |
| 3,652,838 A | 3/1972 | Dillon et al. |
| 3,686,565 A | 8/1972 | Kelem et al. |
| 3,697,870 A | 10/1972 | Brenner |
| 3,704,414 A | 11/1972 | Herbst |
| 3,708,686 A | 1/1973 | Butler, Jr. et al. |
| 3,733,471 A | 5/1973 | Gilberg |
| 3,736,510 A | 5/1973 | Wu |
| 3,742,353 A | 6/1973 | Parisi |
| 3,743,940 A | 7/1973 | Yamagata |
| 3,745,380 A | 7/1973 | Kitajima et al. |
| 3,750,014 A | 7/1973 | Gaw |
| 3,755,734 A | 8/1973 | Blanyer |
| 3,761,740 A | 9/1973 | Naïve |
| 3,766,818 A | 10/1973 | Prohofsky |
| 3,775,681 A | 11/1973 | Konrad |
| 3,777,121 A | 12/1973 | Jamieson |
| 3,780,346 A | 12/1973 | Gagnon |
| 3,795,771 A | 3/1974 | Gundersen et al. |
| 3,803,487 A | 4/1974 | Iten |
| 3,812,427 A | 5/1974 | Coulter |
| 3,823,374 A | 7/1974 | Dandliker et al. |
| 3,838,338 A | 9/1974 | Khoury |
| 3,875,518 A | 4/1975 | Odams |
| 3,930,199 A | 12/1975 | Valis |
| 3,942,123 A | 3/1976 | Georgi |
| 3,943,460 A | 3/1976 | Arai |
| 4,041,387 A | 8/1977 | Dalichow et al. |
| 4,051,434 A | 9/1977 | Sweet |
| 4,053,839 A | 10/1977 | Knoedl |
| 4,063,169 A | 12/1977 | Palmer |
| 4,130,799 A | 12/1978 | Cherry |
| 4,137,497 A | 1/1979 | Lowenschuss |
| 4,139,819 A | 2/1979 | Worley |
| 4,139,870 A | 2/1979 | Tachi |
| 4,144,490 A | 3/1979 | Stevens |
| 4,150,432 A | 4/1979 | Sorden |
| 4,169,213 A | 9/1979 | Dye et al. |
| 4,310,891 A | 1/1982 | Niki |
| 4,339,722 A | 7/1982 | Sydor et al. |
| 4,345,206 A | 8/1982 | Skalka |
| 4,368,354 A | 1/1983 | Furihata et al. |
| 4,374,358 A | 2/1983 | Hirose |
| 4,389,642 A | 6/1983 | Kahn |
| 4,420,809 A | 12/1983 | Pierce |
| 4,494,067 A | 1/1985 | Barszczewski |
| 4,514,592 A | 4/1985 | Miyaguchi |
| 4,544,892 A | 10/1985 | Kaufman et al. |
| 4,546,490 A | 10/1985 | Miller-Thomson et al. |
| 4,583,211 A | 4/1986 | Nishikawa et al. |
| 4,588,979 A | 5/1986 | Adams |
| 4,603,292 A | 7/1986 | Russell |
| 4,609,990 A | 9/1986 | Sember et al. |
| 4,616,173 A | 10/1986 | Cook et al. |
| 4,651,089 A | 3/1987 | Haigh |
| 4,667,689 A | 5/1987 | Kohashi |
| 4,670,712 A | 6/1987 | Lavergnat et al. |
| 4,672,556 A | 6/1987 | Shepler |
| 4,695,791 A | 9/1987 | Miller |
| 4,695,792 A | 9/1987 | Roy |
| 4,707,653 A | 11/1987 | Wagner |
| 4,716,363 A | 12/1987 | Dukes et al. |
| 4,760,536 A | 7/1988 | Curtis |
| 4,769,836 A | 9/1988 | Aihara |
| 4,795,963 A | 1/1989 | Ueno et al. |
| 4,864,588 A | 9/1989 | Simpson et al. |
| 4,864,634 A | 9/1989 | Nakagawa et al. |
| 4,866,260 A | 9/1989 | Lescourret |
| 4,880,005 A | 11/1989 | Pless et al. |
| 4,942,365 A | 7/1990 | Satterwhite |
| 4,984,254 A | 1/1991 | Thomas |
| 5,027,228 A | 6/1991 | Yokoyama |
| 5,065,095 A | 11/1991 | Suzuki |
| 5,095,279 A | 3/1992 | Quan et al. |
| 5,122,758 A | 6/1992 | Tomita |
| 5,128,607 A * | 7/1992 | Clark et al. ............... 324/76.47 |
| 5,157,699 A | 10/1992 | Miyazaki et al. |
| 5,168,215 A | 12/1992 | Puzzo |
| 5,206,549 A | 4/1993 | Suzuki et al. |
| 5,262,714 A | 11/1993 | Friedman |
| 5,302,916 A | 4/1994 | Pritchett |
| 5,304,938 A | 4/1994 | Gregory et al. |
| 5,313,154 A | 5/1994 | Norris |
| 5,317,215 A | 5/1994 | Kranzler |
| 5,323,096 A | 6/1994 | Nakai |
| 5,365,181 A | 11/1994 | Mair |
| 5,381,085 A * | 1/1995 | Fischer ..................... 324/76.48 |
| 5,442,278 A * | 8/1995 | Chiang et al. ............. 324/76.41 |
| 5,448,606 A | 9/1995 | Snelgrove |
| 5,471,133 A | 11/1995 | Sezi |
| 5,509,040 A | 4/1996 | Shimada |
| 5,539,355 A | 7/1996 | Nakamura |
| 5,555,247 A | 9/1996 | Matsuoka et al. |
| 5,650,954 A | 7/1997 | Minuhin |
| 5,652,552 A * | 7/1997 | Chung ........................ 332/104 |
| 5,710,710 A | 1/1998 | Owen et al. |
| 5,764,045 A | 6/1998 | Hayashi |
| 5,941,974 A * | 8/1999 | Babin ......................... 710/316 |
| 6,018,560 A | 1/2000 | Kim |
| 6,078,200 A | 6/2000 | Miyano |
| 6,127,950 A * | 10/2000 | Yamauchi ..................... 341/55 |
| 6,140,869 A | 10/2000 | Troise |
| 6,172,579 B1 * | 1/2001 | Dacus et al. ................. 332/128 |
| 6,181,829 B1 | 1/2001 | Clark et al. |
| 6,259,251 B1 | 7/2001 | Sugiura et al. |
| 6,265,869 B1 | 7/2001 | Takahashi |
| 6,282,803 B1 | 9/2001 | Dunne |
| 6,359,938 B1 | 3/2002 | Keevill et al. |
| 6,360,090 B1 | 3/2002 | Holcombe et al. |
| 6,377,616 B1 | 4/2002 | Brankovic et al. |
| 6,411,075 B1 | 6/2002 | Battiston et al. |
| 6,463,452 B1 | 10/2002 | Schulist |
| 6,519,194 B2 * | 2/2003 | Tsujino et al. ............... 365/201 |
| 6,549,479 B2 * | 4/2003 | Blodgett ..................... 365/222 |
| 6,566,964 B1 | 5/2003 | Hirano |
| 6,590,400 B2 | 7/2003 | Hilliard et al. |
| 6,665,367 B1 | 12/2003 | Blair |
| 6,674,277 B1 | 1/2004 | Oishi et al. |
| 6,675,326 B1 | 1/2004 | Yoshizaki |
| 6,680,607 B2 | 1/2004 | Smith |
| 6,759,838 B2 | 7/2004 | Tao et al. |
| 6,834,093 B1 | 12/2004 | Chiu |
| 6,888,902 B1 | 5/2005 | Kondo |
| 6,917,191 B2 | 7/2005 | Oishi et al. |
| 7,027,940 B2 | 4/2006 | Iannuzzi |
| 7,046,964 B1 | 5/2006 | Sullivan et al. |
| 7,068,744 B2 | 6/2006 | Watanabe |
| 7,124,153 B2 | 10/2006 | Grushin |
| 7,230,458 B2 | 6/2007 | DaDalt |
| 7,242,223 B1 | 7/2007 | Alon |
| 7,265,559 B1 | 9/2007 | Hladky et al. |
| 7,266,756 B2 | 9/2007 | Saado et al. |
| 7,271,631 B2 | 9/2007 | Watanabe |
| 7,276,978 B2 | 10/2007 | Puma et al. |
| 7,285,961 B2 | 10/2007 | Shinmoto et al. |
| 7,372,875 B2 | 5/2008 | Hadzic et al. |
| 7,394,723 B2 | 7/2008 | Rubin |
| 7,409,031 B1 | 8/2008 | Lee et al. |
| 7,429,896 B2 | 9/2008 | Hattori |
| 7,436,265 B2 | 10/2008 | Park et al. |
| 7,463,096 B2 * | 12/2008 | Chi et al. ....................... 331/2 |
| 7,466,789 B2 | 12/2008 | Rieubon et al. |
| 7,504,976 B1 | 3/2009 | Pellon |
| 7,560,962 B2 | 7/2009 | Kamath |
| 7,636,747 B2 | 12/2009 | Watanabe |
| 7,642,767 B2 | 1/2010 | Willis |
| 7,653,170 B2 | 1/2010 | Mattes et al. |
| 7,692,419 B1 | 4/2010 | Peel |
| 7,696,741 B2 | 4/2010 | Gurr |
| 7,729,071 B2 | 6/2010 | Harada |
| 7,737,688 B2 | 6/2010 | Tomida et al. |

(56) References Cited

U.S. PATENT DOCUMENTS

| | | | |
|---|---|---|---|
| 7,750,618 B1 | 7/2010 | Fang et al. |
| 7,750,685 B1 | 7/2010 | Bunch |
| 7,804,289 B2 | 9/2010 | Li |
| 7,847,597 B1 | 12/2010 | Chan et al. |
| 7,907,016 B2 | 3/2011 | Eikenbroek |
| 7,932,751 B2 | 4/2011 | Boomer |
| 8,139,685 B2 | 3/2012 | Simic et al. |
| 8,140,283 B2 | 3/2012 | Benmouyal et al. |
| 8,242,941 B2 | 8/2012 | Arknaes-Pedersen et al. |
| 8,258,831 B1 | 9/2012 | Banai et al. |
| 8,461,821 B2 | 6/2013 | Todorokihara |
| 8,508,213 B2 | 8/2013 | Todorokihara |
| 2001/0045868 A1 | 11/2001 | Takeyabu et al. |
| 2001/0048348 A1 | 12/2001 | Unterricker |
| 2002/0024343 A1 | 2/2002 | Moore |
| 2002/0097091 A1 | 7/2002 | Takagishi |
| 2002/0167874 A1 | 11/2002 | Hayashi |
| 2002/0180415 A1 | 12/2002 | Roth |
| 2003/0038624 A1 | 2/2003 | Hilliard et al. |
| 2003/0046064 A1 | 3/2003 | Moriya et al. |
| 2003/0165112 A1 | 9/2003 | Noda |
| 2003/0176932 A1 | 9/2003 | Wild |
| 2003/0184346 A1 | 10/2003 | Lamb |
| 2003/0215100 A1 | 11/2003 | Kimura et al. |
| 2004/0075425 A1 | 4/2004 | Horio et al. |
| 2004/0078737 A1 | 4/2004 | Miyamoto |
| 2004/0196052 A1 | 10/2004 | Okayasu |
| 2004/0199345 A1 | 10/2004 | Ananthanarayanan et al. |
| 2005/0025270 A1 | 2/2005 | Muhammad et al. |
| 2005/0110500 A1 | 5/2005 | Hoyte et al. |
| 2005/0147197 A1 | 7/2005 | Perrott |
| 2005/0237125 A1 | 10/2005 | Hino |
| 2005/0270043 A1 | 12/2005 | Iacob et al. |
| 2006/0084386 A1 | 4/2006 | Irie et al. |
| 2006/0120537 A1 | 6/2006 | Burnett et al. |
| 2006/0171496 A1 | 8/2006 | Nakamuta et al. |
| 2006/0246865 A1 | 11/2006 | Makarov |
| 2006/0267698 A1 | 11/2006 | Erdogan et al. |
| 2006/0285756 A1 | 12/2006 | Sugita |
| 2007/0094581 A1 | 4/2007 | Kajita |
| 2007/0103333 A1 | 5/2007 | Michaiski et al. |
| 2007/0132442 A1 | 6/2007 | Jones |
| 2007/0159938 A1* | 7/2007 | Sugawara et al. .......... 369/44.26 |
| 2007/0216556 A1 | 9/2007 | Rieubon et al. |
| 2008/0019471 A1 | 1/2008 | Waldner |
| 2008/0068096 A1* | 3/2008 | Feng et al. ........ 331/18 |
| 2008/0104072 A1 | 5/2008 | Stampleman et al. |
| 2008/0122498 A1 | 5/2008 | Furukawa |
| 2008/0136471 A1 | 6/2008 | Kamath |
| 2008/0165862 A1 | 7/2008 | Takahashi |
| 2008/0189064 A1 | 8/2008 | Yamaguchi et al. |
| 2008/0191762 A1 | 8/2008 | Seethamraju et al. |
| 2008/0204088 A1 | 8/2008 | Garlapati et al. |
| 2008/0229829 A1* | 9/2008 | Kondo ................ 73/579 |
| 2008/0247500 A1 | 10/2008 | Goto et al. |
| 2008/0291287 A1 | 11/2008 | Dvir |
| 2008/0320065 A1 | 12/2008 | Kan |
| 2009/0058452 A1 | 3/2009 | Tanaka et al. |
| 2009/0058468 A1 | 3/2009 | Hjelm et al. |
| 2009/0144018 A1 | 6/2009 | Chang et al. |
| 2009/0153256 A1 | 6/2009 | Jo et al. |
| 2009/0156150 A1* | 6/2009 | Deleon ............ 455/260 |
| 2009/0180527 A1 | 7/2009 | Asami |
| 2009/0192958 A1 | 7/2009 | Todorokihara |
| 2009/0237070 A1 | 9/2009 | Herselman |
| 2009/0240994 A1 | 9/2009 | Lee |
| 2009/0243736 A1 | 10/2009 | Miura et al. |
| 2009/0251129 A1 | 10/2009 | Todorokihara et al. |
| 2009/0261809 A1 | 10/2009 | Li |
| 2009/0295460 A1 | 12/2009 | Gulba et al. |
| 2009/0296878 A1 | 12/2009 | Tsai |
| 2010/0052653 A1 | 3/2010 | Lebrun |
| 2010/0054390 A1 | 3/2010 | Kim et al. |
| 2010/0091752 A1 | 4/2010 | Kemmochi et al. |
| 2010/0213924 A1 | 8/2010 | Osumi et al. |
| 2010/0289479 A1 | 11/2010 | Prance et al. |
| 2010/0295535 A1 | 11/2010 | Todorokihara |
| 2010/0295536 A1 | 11/2010 | Todorokihara |
| 2010/0295537 A1 | 11/2010 | Todorokihara |
| 2010/0315061 A1 | 12/2010 | Tomita et al. |
| 2011/0068828 A1 | 3/2011 | Anderson et al. |
| 2011/0074514 A1 | 3/2011 | Marutani |
| 2011/0082656 A1 | 4/2011 | Todorokihara |
| 2011/0084687 A1 | 4/2011 | Todorokihara |
| 2011/0150168 A1 | 6/2011 | Tseng et al. |
| 2011/0182398 A1 | 7/2011 | Iwashita et al. |
| 2011/0235772 A1 | 9/2011 | Obkircher |
| 2012/0019301 A1 | 1/2012 | Murray |
| 2012/0053903 A1 | 3/2012 | Todorokihara |
| 2012/0161815 A1 | 6/2012 | Polivka |

FOREIGN PATENT DOCUMENTS

| | | |
|---|---|---|
| JP | A-61-501528 | 7/1986 |
| JP | A-61-223662 | 10/1986 |
| JP | A-62-298726 | 12/1987 |
| JP | A-64-054271 | 3/1989 |
| JP | A-64-57189 | 3/1989 |
| JP | A-02-252306 | 10/1990 |
| JP | A-04-048271 | 2/1992 |
| JP | A-04-072815 | 3/1992 |
| JP | A-04-357468 | 12/1992 |
| JP | A-05-030772 | 4/1993 |
| JP | A-05-172861 | 7/1993 |
| JP | A-05-327515 | 12/1993 |
| JP | A-06-011525 | 1/1994 |
| JP | A-06-501554 | 2/1994 |
| JP | A-06-164372 | 6/1994 |
| JP | A-06-235743 | 8/1994 |
| JP | A-06-342021 | 12/1994 |
| JP | A-07-055554 | 3/1995 |
| JP | A-07-229910 | 8/1995 |
| JP | A-07-260526 | 10/1995 |
| JP | A-09-304259 | 11/1997 |
| JP | A-10-132874 | 5/1998 |
| JP | A-10-170566 | 6/1998 |
| JP | A-09-178785 | 7/1998 |
| JP | A-11-220369 | 8/1999 |
| JP | A-11-264846 | 9/1999 |
| JP | A-2001-094395 | 4/2001 |
| JP | A-2001-119291 | 4/2001 |
| JP | A-2001-166008 | 6/2001 |
| JP | A-2001-177378 | 6/2001 |
| JP | A-2003-065768 | 3/2003 |
| JP | A-2003-194860 | 7/2003 |
| JP | A-2003-249905 | 9/2003 |
| JP | A-2003-307481 | 10/2003 |
| JP | A-2003-315356 | 11/2003 |
| JP | A-2005-020554 | 1/2005 |
| JP | A-2006-029874 | 2/2006 |
| JP | A-2007-060447 | 3/2007 |
| JP | A-2008-131500 | 6/2008 |
| JP | A-2009-229353 | 10/2009 |
| JP | A-2009-250807 | 10/2009 |
| JP | A-2009-250808 | 10/2009 |
| JP | A-2010-085286 | 4/2010 |
| JP | A-2010-127914 | 6/2010 |
| JP | A-2010-271210 | 12/2010 |
| JP | A-2010-271211 | 12/2010 |
| WO | WO 85-04487 A | 10/1985 |
| WO | WO 92/04634 A1 | 3/1992 |

OTHER PUBLICATIONS

Oct. 11, 2011 Office Action issued in U.S. Appl. No. 12/418,000.
Office Action issued Dec. 14, 2011 in U.S. Appl. No. 12/782,382.
Office Action issued Dec. 29, 2011 in U.S. Appl. No. 12/783,900.
Office Action issued Jan. 6, 2012 in U.S. Appl. No. 12/784,136.
Feb. 29, 2012 Office Action issued in U.S. Appl. No. 12/782,382.
Mar. 7, 2012 Office Action issued in U.S. Appl. No. 12/418,000.
Office Action dated May 25, 2012 issued in U.S. Appl. No. 12/782,382.
Office Action dated May 30, 3012 issued in U.S. Appl. No. 12/783,900.

(56) References Cited

OTHER PUBLICATIONS

Office Action dated May 23, 2012 issued in U.S. Appl. No. 12/784,136.
Office Action dated Jun. 5, 2012 issued in U.S. Appl. No. 12/418,000.
Jul. 31, 2012 Office Action issued in U.S. Appl. No. 12/418,000.
Sep. 27, 2012 Office Action Issued in U.S. Appl. No. 12/783,900.
Sep. 14, 2012 Office Action issued in U.S. Appl. No. 12/784,136.
Oct. 17, 2012 Office Action issued in U.S. Appl. No. 12/889,770.
U.S. Appl. No. 12/783,900 in the name of Todorokihara, filed on May 20, 2010.
U.S. Appl. No. 12/889,770 in the name of Todorokihara, filed on Sep. 24, 2010.
U.S. Appl. No. 12/784,136 in the name of Todorokihara, filed on May 20, 2010.
U.S. Appl. No. 12/782,382 in the name of Todorokihara, filed on May 18, 2010.
U.S. Appl. No. 12/418,000 in the name of Todorokihara, filed on Apr. 3, 2009.
U.S. Appl. No. 12/896,106 in the name of Todorokihara, filed on Oct. 1, 2010.
U.S. Appl. No. 13/211,726 in the name of Todorokihara, filed on Aug. 17, 2011.
Nov. 13, 2012 Office Action issued in U.S. Appl. No. 12/896,106.
Nov. 28, 2012 Office Action issued in U.S. Appl. No. 12/418,000.
Nov. 30, 2012 Notice of Allowance issued in U.S. Appl. No. 12/782,382.
Feb. 6, 2013 Notice of Allowance issued in U.S. Appl. No. 12/784,136.
Jan. 14, 2013 Advisory Action issued in U.S. Appl. No. 12/783,900.
Jan. 28, 2013 Office Action issued in U.S. Appl. No. 12/783,900.
Jan. 31, 2013 Office Action issued in U.S. Appl. No. 12/889,770.
Mar. 13, 2013 Notice of Allowance issued in U.S. Appl. No. 12/782,382.
Apr. 19, 2013 Notice of Allowance issued in U.S. Appl. No. 12/889,770.
Jun. 12, 2013 Notice of Allowance issued in U.S. Appl. No. 12/783,900.
Jul. 8, 2013 Office Action issued in U.S. Appl. No. 12/896,106.
Jul. 16, 2013 Notice of Allowance issued in U.S. Appl. No. 12/889,770.
Jul. 11, 2013 Corrected Notice of Allowability issued in U.S. Appl. No. 12/782,382.
Sep. 25, 2013 Office Action Issued in U.S. Appl. No. 13/211,726.
Nov. 22, 2013 Notice of Allowance issued in U.S. Appl. No. 12/896,106.

\* cited by examiner

ELECTRIC CIRCUIT, SENSOR SYSTEM EQUIPPED WITH THE ELECTRIC CIRCUIT, AND SENSOR DEVICE EQUIPPED WITH THE ELECTRIC CIRCUIT

The entire disclosure of Japanese Patent Application No. 2009-196512, filed Aug. 27, 2009 is expressly incorporated by reference herein.

BACKGROUND

1. Technical Field

The present invention relates to sensor systems using oscillators, electric circuits used for the sensor systems, and sensor devices equipped with the electric circuits.

2. Related Art

There is a phenomenon in which, when substance included in a surrounding medium adheres to the surface of a crystal vibrator that is in a resonance state, the resonance frequency changes according to the adhered substance. A technology using such a phenomenon is called QCM (Quarts Crystal Microbalance), and used in sensors for detecting the presence or the amount of molecules included in an ambient medium. As application examples of QCM, odor sensors made of vibratos with adsorption films formed thereon for selectively adsorbing specified molecules on the surfaces of the vibrators may be enumerated. Also, applications of QCM to biosensors using hybridization of DNA, gas sensors and the like are under consideration.

In general, AT-cut crystal vibrators are used for QCM devices. The AT-cut refers to a cut substrate in a specific crystal orientation with respect to the quartz crystal axis, and is widely used without being limited to QCM devices because changes in its temperature coefficient adjacent to room temperature are extremely small and it has excellent temperature stability.

An AT-cut crystal vibrator is made of a substrate having excitation electrodes formed on front and back surfaces thereof and operates in a so-called thickness shear vibration mode in which the front surface and the back surface move in opposite directions upon application of a voltage between the electrodes. Its resonance frequency $f_0$ is in reverse proportion to the thickness of the crystal plate at a portion interposed between the front and back electrodes, and generally has the following relation.

$$f_0(MHz) = 1670/\text{the thickness of crystal plate}(\mu m)$$

It is known that the relation between changes in the oscillation frequency $\Delta f$ of the QCM device using such an AT-cut crystal vibrator and the mass $\Delta M$ adsorbed on the crystal vibrator is expressed by the following Sauerbrey equation.

$$\Delta f = -\frac{2 \times f_0^2}{\sqrt{\rho \times \mu}} \times \frac{\Delta M}{A} \qquad \text{[Equation 1]}$$

Where $f_0$ is a resonant frequency of the vibrator, $\rho$ is the density of quartz, $\mu$ is the shear modulus of quartz, and A is an effective vibration area (i.e., generally equal to the electrode area). It is understood from the equation above that the sensitivity, in other words, the change in the oscillation frequency $\Delta f$ per the adsorbed mass $\Delta M$ can be increased by increasing the resonance frequency $f_0$ of the quartz vibrator.

The above-described quartz vibrator per se relatively excels in temperature stability. However, as changes in the frequency caused by adsorption of substance to be measured by a QCM device are extremely small, small changes in the frequency that may be caused by jitters in the ambient temperature, localized unevenness in the viscosity and density of a solution when a liquid is a measuring environment, and the like, which are generally referred to as drifts, would pose problems.

To correct such drifts, for example, Japanese Laid-open Patent Application 2003-307481 (Patent Document 1) describes a QCM device equipped with a plurality of sensors, which is provided with vibrators with adsorption films formed thereon, and vibrators without adsorption films formed thereon adjacent to the vibrators with the adsorption films. A difference between two frequencies for a test channel and a correction channel is used as a detection value, thereby cancelling drift errors common to both of the channels.

However, the method of cancelling drift errors described above entails some problems. For example, an absolute value of the frequency for each channel needs to be measured, which requires a high measuring accuracy for each channel, whereby a counter circuit as a frequency measuring equipment becomes more complex.

SUMMARY

In accordance with an advantage of some aspects of the invention, it is possible to provide a sensor system that is structured to be capable of removing influence of drifts with a simpler composition.

In accordance with an embodiment of the invention, an electric circuit includes a reference signal generation circuit that generates a reference signal based on a first oscillation signal that is an oscillation signal of a first oscillation circuit that vibrates a first vibrator, and a counter circuit that counts a second oscillation signal that is an oscillation signal of a second oscillation circuit that vibrates a second vibrator based on the reference signal, and outputs a count signal, the count signal is a change of the count value of the second oscillation signal.

According to such a structure, the frequencies of the first oscillation signal and the second oscillation signal increase or decrease at the same ratio. Also, the counter circuit uses the relative relation between the first oscillation signal and the second oscillation signal that increase or decrease at the same ratio according to a change in the surrounding environment, and performs counting while mutually cancelling the increase or decrease in the frequencies of the oscillation signals. Therefore, the count signal counted by the counter circuit is not affected by drifts due to the relation between the first oscillation signal and the second oscillation signal, such that substance included in a surrounding medium can be properly detected regardless of changes in the surrounding environment. Further, without obtaining an absolute value of the frequency of each of the oscillation signals, it is possible to obtain a change amount in the frequency of the first oscillation signal necessary to detect substance included in a surrounding medium. As a result, a simple and small electric circuit can be structured without using a frequency measuring apparatus with high accuracy or an operation circuit for cancelling drifts.

Also, the first vibrator and the second vibrator may preferably be provided on a common substrate. By this structure, the first vibrator and the second vibrator can be disposed spatially close to each other. Accordingly, influence by a temperature difference or the like, which may be caused if the first vibrator and the second vibrator are spatially separated far from each other, can be suppressed to a minimum.

Also, the reference signal generation circuit may preferably generate a reference signal having a frequency lower than that of the first oscillation signal.

Also, the counter circuit may preferably be further equipped with an initial stage counter circuit that counts a pulse number of the second oscillation signal, a latch circuit that obtains a count value of the initial stage counter circuit synchronizing with the reference signal, and an operation circuit that calculates a difference between a first count value newly obtained by the latch circuit and a second count value previously obtained by the latch circuit and outputs the difference as the count signal.

According to the structure described above, the counter circuit can thoroughly count changes in the amplitude of the second oscillation signal, and therefore can more accurately detect substance included in a surrounding medium.

Also, the initial stage counter circuit may preferably be structured in a manner that only one bit of the count value changes at the time of count-up.

In the latch circuit, when a count value is obtained while the count value of the initial stage counter circuit is in transition from a value before count-up to a value after count-up, there may be an occasion in which a value before count-up may be acquired at a certain bit in the count value composed of multiple bits, and a value after count-up may be acquired at another bit in the multiple bits. In this case, depending on the structure of the initial counter circuit, a series of count values obtained by the latch circuit may be completely different from either of the values before and after count-up, whereby a so-called static hazard occurs. In this respect, according to the structure described above, a difference in the series of count values acquired by the latch circuit is confined within the range of a LSB at most. In other words, the latch circuit would hardly be affected even if the count value of the initial stage counter circuit is obtained in transition from a value before count-up to a value after count-up. This makes it possible to avoid static hazards that can occur in the counter circuit.

Also, the counter circuit may preferably be further equipped with a low-pass filter circuit that removes high frequency components in the count signal outputted from the operation circuit.

According to the structure described above, low-frequency components included in the count signal can be effectively extracted, and frequency variation information included in the second oscillation signal can be effectively obtained.

Further, the reference signal may preferably have a frequency that is 100 or more times the frequency of a time variation component of the frequency of the second oscillation signal.

In order to properly sample a time variation component of the frequency of the second oscillation signal, a signal having a frequency that satisfies the sampling theorem, which is a signal having a frequency at least twice the time variation component of the frequency of the second oscillation signal, may preferably be used as a reference signal. With the structure equipped with the low-pass filter described above, oversampling may be performed with a signal having a frequency considerably higher than the aforementioned frequency, for example, a signal having a frequency 100 or more times the time variation component of the frequency of the second oscillation signal as a reference signal, whereby the so-called noise shaping effect is more effectively utilized, and frequency variation information contained in the second oscillation signal can be obtained with higher resolving power and higher S/N ratio. According to the structure described above, the reference signal has a frequency 100 or more times the frequency of a time variation component of the frequency of the second oscillation signal, such that frequency variation information included in the second oscillation signal can be obtained with sufficiently high resolving power and S/N ratio.

Also, the reference signal may preferably have a frequency of 100 Hz or higher.

According to such a structure, empirically, frequency variation information included in the second oscillation signal can be obtained with sufficiently high resolving power. It is empirically known that the frequency of a time variation component of the frequency of the second oscillation signal, in other words, the time variation frequency in QCM response as an odor sensor is at about several Hz at maximum. If oversampling that sufficiently brings out the aforementioned noise shaping effect is to be performed, a reference signal having a frequency that is at least several 100 times the aforementioned several Hz, in other words, at about several 100 Hz or higher may preferably be used. More preferably, a reference signal having a frequency at 1 kHz or higher may be used. The higher the gate clock frequency, the move the frequency resolving power and S/N ratio improve. However, suitable frequencies need to be selected in consideration of issues relating to operation accuracy and power consumption accompanying higher frequency implementation of circuits.

Also, the counter circuit may preferably output the count signal at a period of a predetermined multiple (for example, several ten times or more) of the period of the reference signal.

According to such a structure, the count signal to be outputted from the counter circuit can be cropped and outputted, and therefore the power consumption of the electric circuit can be reduced. Also, it becomes possible to reduce the power consumption of a data processing circuit for processing the count signal or the like that is connected to the electric circuit, and reduce the circuit scale. As the frequency of the reference signal is increased, not only the frequency resolving power but also the time-resolving power is increased. This means that the data output frequency becomes higher, which may cause a problem of an increased load for data processing. On the other hand, it is empirically known that the frequency of a time variation component of the frequency of the second oscillation signal, in other words, the time variation frequency in QCM response as an odor sensor is about several Hz at maximum, and it can be said that a data capturing frequency four times greater than such time variation frequency is enough to measure the same. Accordingly, cropping the output data lowers the time-resolving power but does not practically cause any problem, whereby the data processing load can be reduced. As the necessary data output cycle is at about several Hz, the frequency of the reference signal may preferably be frequency-divided to be cropped to a cycle with a quarter of the oversampling coefficient of several 100 times, in other words, an oversampling coefficient of several ten times. Simply cropping with a predetermined multiple also makes the circuit simpler.

In accordance with an embodiment of the invention, a sensor system having any one of the electric circuits described above, a database that is input relations between changes of the frequency of the second oscillation signal and a plurality of substances contained in a medium existing around the second vibrator, and a data processing circuit that specifies one of the plurality of substances contained in the medium based on the count signal outputted from the electric circuit and the database.

Because the sensor system having the structure described above is equipped with one of the electric circuits described above, it is possible to form a sensor system equipped with a simple and small-sized electric circuit without using, for example, a frequency measurement apparatus with high accuracy.

Also, in the sensor system, the count signal outputted from the counter circuit may be a parallel signal, and the sensor system may preferably be further equipped with a parallel-serial converter circuit that converts the count signal to a serial signal and outputs the same.

According to the sensor system having the structure described above, the number of wirings between the counter circuit and the data processing circuit can be substantially reduced, and the sensor system with a simplified structure can be made.

Furthermore, in accordance with another aspect of the embodiment of the invention, the first vibrator and the second vibrator are provided on a common substrate.

Moreover, in accordance with still another aspect of the embodiment of the invention, a sensor device is equipped with any one of the electric circuits described above, the first oscillation circuit including the first vibrator, and the second oscillation circuit including the second vibrator, wherein the first vibrator and the second vibrator are provided on a common substrate.

DESCRIPTION OF EXEMPLARY EMBODIMENTS

Embodiments of the invention are concretely described below, according to the following composition, with reference to the accompanying drawings. It should be understood, however, that the following embodiments are merely examples of the invention, and do not limit the technical range of the invention. It is noted that identical parts in the drawings will be appended with the same reference numbers, and their description may be omitted if appropriate.

1. Definition
2. Embodiment 1
(1) Structure of Sensor System
(2) Operation of Sensor System
(3) Characteristics of Embodiment 1
3. Embodiment 2
(1) Structure and Operation of Sensor System
(2) Characteristics of Embodiment 2
4. Embodiment 3
(1) Structure and Operation of Sensor System
(2) Characteristics of Embodiment 3
5. Supplementation 1. Definition First, terms used in this specification are defined as follows.

Any circuits or use of circuits means an electrical circuit without any particular limitation thereto, and may also include a physical means that achieves the function of the circuit or a functional mean that is realized by software. Also, the function of one section may be realized by two or more physical means or functional means, or the function of two or more sections may be realized by one physical mean or one functional mean.

An "electronic apparatus" includes any and every apparatus equipped with a sensor system described in the present specification, and may include odor sensors, alcohol sensors, narcotics detectors and the like.

2. Embodiment 1

An embodiment of the invention pertains to a sensor system using vibrators, and is characterized by an electric circuit used in the system. The embodiment will be described in detail below with reference to FIGS. 1 through 3.

(1) Structure of Sensor System

Figure 1:
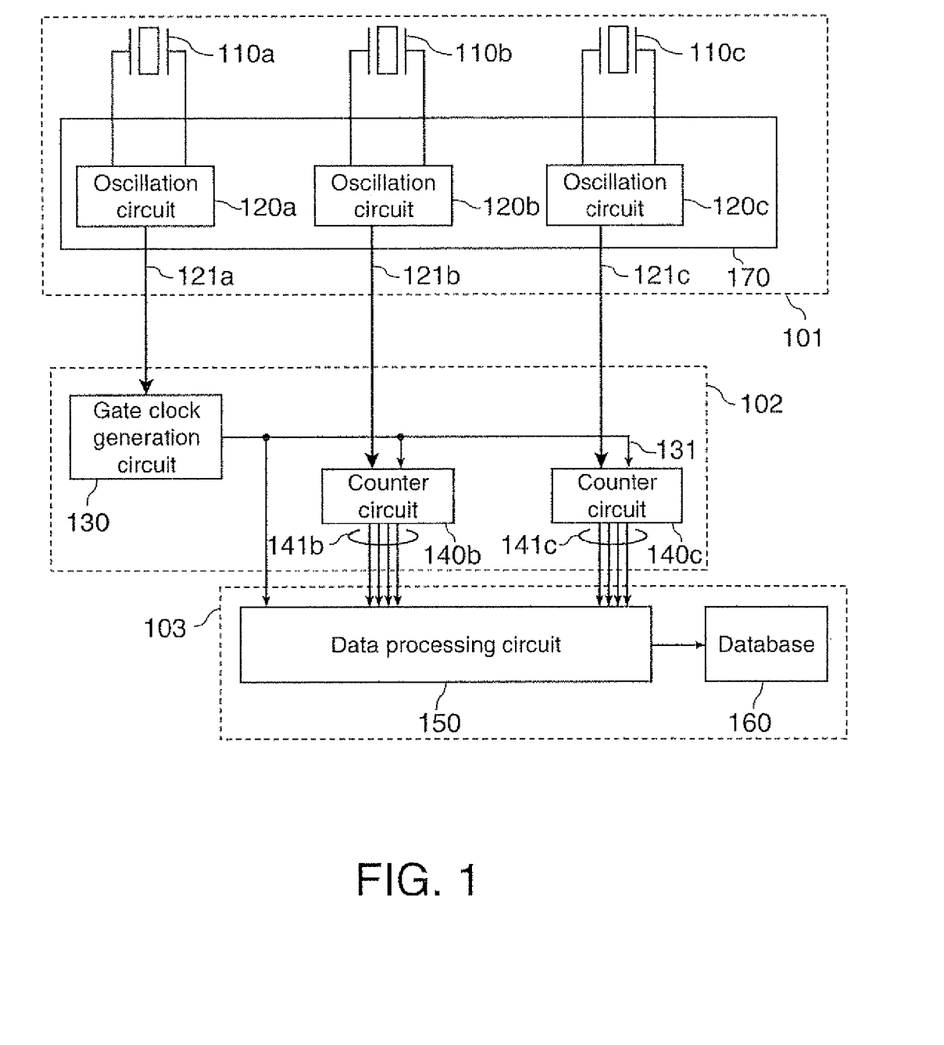
FIG. 1 is a diagram showing a structure example of a sensor system in accordance with Embodiment 1.

FIG. 1 is a diagram showing a structure example of a sensor system in accordance with an embodiment of the invention. As shown in FIG. 1, the sensor system in accordance with the present embodiment includes crystal vibrators $110a$-$110c$, oscillation circuits $120a$-$120c$, a gate clock generation circuit 130, counter circuits $140b$ and $140c$, a data processing circuit 150, and a database 160. It is noted that the plural oscillation circuits $120a$-$120c$ are formed on a common substrate 170. The plural crystal vibrators $110a$-$110c$ connected respectively to the plural oscillation circuits $120a$-$120c$ are provided on the substrate 170. It is noted, as shown in FIG. 1, that the sensor system may be divided into an oscillation circuit section 101, an electric circuit 102, and a computer 103. The oscillation circuit section 101 is equipped with the crystal vibrators $110a$-$110c$ and the oscillation circuits $120a$-$120c$. The electric circuit 102 is equipped with the gate clock generation circuit 130 and the counter circuits $140b$ and $140c$. The computer 103 is equipped with the data processing circuits 150 and 160. In this example, a structure including the oscillation circuit section 101 and the electric circuit 102 may be called a sensor device. Also, the sensor system refers to a system that is equipped at least with the electric circuit 102 and the computer 103, and may not necessarily include the oscillation circuit section 101.

Crystal Vibrators $110a$-$110c$

Each of the crystal vibrators $110a$-$110c$ has a pair of electrodes formed on their front surface and back surface, and is connected to each of the oscillation circuits $120a$-$120c$, respectively, through the electrode pair. Also, the crystal vibrators $110a$-$110c$ are formed on the same substrate. The crystal vibrators $110a$-$110c$ each operate in a so-called thickness shear vibration mode in which the front surface and the back surface move in opposite directions upon application of a voltage between the electrode pair.

The electrodes of the crystal vibrators $110b$ and $110c$ are equipped on their surfaces with adsorption films having a characteristic that selectively adsorbs specific substance, and are exposed to an ambient medium (including gas and liquid) containing substance to be detected. The adsorption films of different kinds are used for each of the crystal vibrators. In FIG. 1, the crystal vibrators $110b$ and $110c$ are equipped with mutually different kinds of adsorption films. However, the crystal vibrator $110a$ connected to the gate clock generation circuit 130 through the oscillation circuit $120a$ is not equipped with an adsorption film. It may be preferred if the crystal vibrator 110a is sealed so as not to be exposed to the open air. The adsorption film may be formed on one or each of the surfaces of the crystal vibrators 110b and 110c, but the adsorption films may preferably be formed on both of the surfaces. Adsorption films formed on both of the surfaces can more effectively adsorb target substance to be adsorbed than an adsorption film formed on one of the surfaces. As the adsorption film, a polymer film, a fat film, a protein film, or a single molecule film may be used. Also, it is preferred that kinds of readily adsorbable molecules may be different depending on the kinds of adsorption films.

Oscillation Circuit 120a-120c

The oscillation circuits 120a-120c are formed on the common substrate 170, and connected to the crystal vibrators 110a-110c, respectively. Also, the oscillation circuits 120a-120c output oscillation signals 121a-121c, respectively. The substrate 170 may be made of, for example, glass epoxy, plastics, or ceramics.

Figure 2:
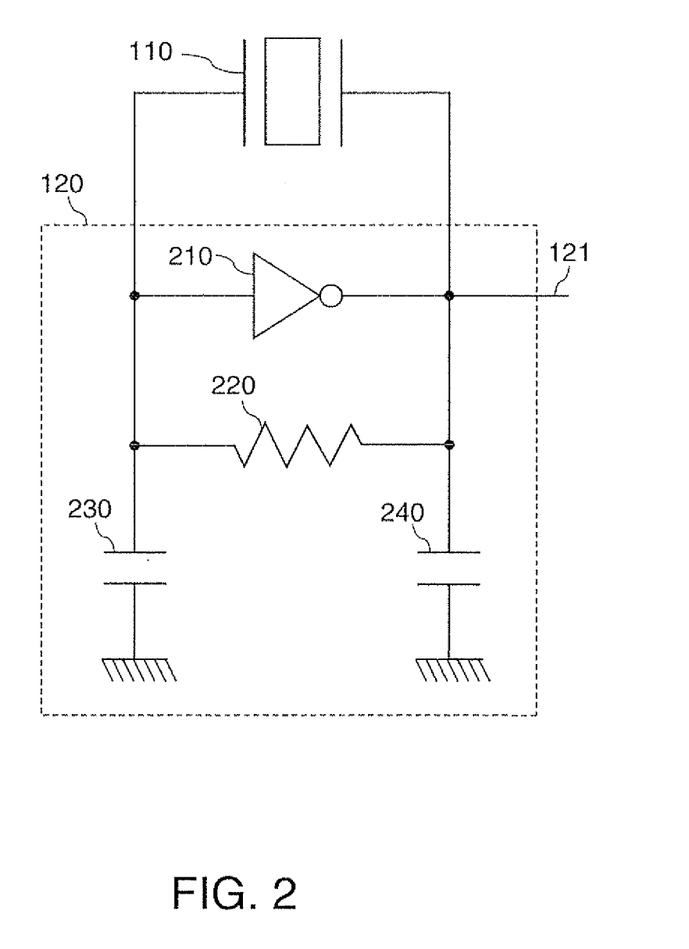
FIG. 2 is a diagram schematically showing a structure example of an oscillation circuit connected to a quartz vibrator.

FIG. 2 is a schematic diagram showing an example structure of the oscillation circuit 120 connected to the crystal vibrators 110. As shown in FIG. 2, the oscillation circuit 120 includes an inverter 210, a feedback resistance 220, added capacitances 230 and 240, and an oscillation signal output wiring 121, thereby forming a so-called Colpitts oscillation circuit. An input terminal of the inverter 210 is connected to a first electrode of the crystal vibrator 110, a first terminal of the feedback resistance 220, and a first terminal of the added capacitance 230; and an output terminal of the inverter 210 is connected to a second electrode of the crystal vibrator 110, a second terminal of the feedback resistance 220, a first terminal of the added capacitance 240, and the oscillation signal output wiring 121. Also the second terminal of the added capacitance 230 and the second terminal of the added capacitance 240 are both connected to the ground potential. It is noted that the terminals of the crystal vibrator 110 do not have polarities, such that their terminals may be inverted without affecting the operation at all.

It is noted that the Colpitts oscillation circuit is only an example, and the oscillation circuit 120 may be composed with any one of other structures.

Gate Clock Generation Circuit 130

The gate clock generation circuit 130 generates a gate clock signal 131 based on the oscillation signal 121a that is an output signal from the oscillation circuit 120a, as shown in FIG. 1. The gate clock signal 131 generated by the gate clock generation circuit 130 is inputted in the data processing circuit 150 and the counter circuits 140b and 140c. It is noted that the gate clock signal 131 is a signal generated by frequency-dividing the oscillation signal 121a at a specified dividing ratio, and is a signal having a lower frequency than that of the oscillation signal 121a. It is noted that the crystal vibrator 110a and the oscillation circuit 120a are provided for generating the gate clock signal 131, and they may also be called a reference vibrator and a reference oscillation circuit, respectively. Also, the gate clock signal 131 may be called a reference signal, and the gate clock generation circuit 130 may also be called a reference signal generation circuit.

Counter Circuits 140b and 140c

Figure 3:
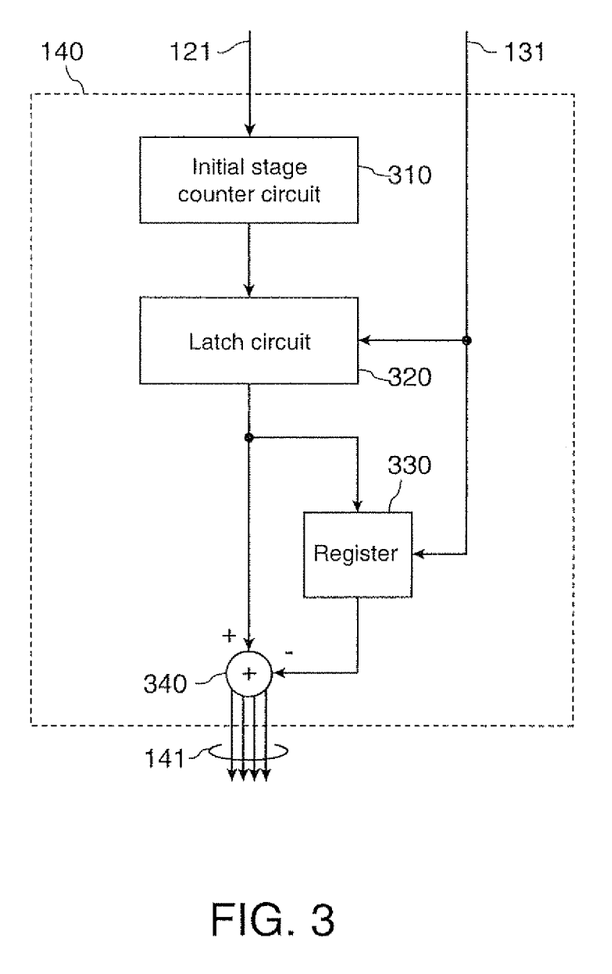
FIG. 3 is a diagram schematically showing a structure example of a counter circuit.

The counter circuits 140b and 140c receive the oscillation signal 121b from the oscillation circuit 120b and the oscillation signal 121c from the oscillation circuit 120c, respectively, and receive the gate clock signal 131 from the gate clock generation circuit 130. The counter circuit 140b counts changes in the oscillation signal 121b based on the oscillation signal 121b and the gate clock signal 131, and outputs the count value as a count signal 141b. The counter circuit 140c similarly counts changes in the oscillation signal 121c based on the oscillation signal 121c and the gate clock signal 131, and outputs the count value as a count signal 141c. Referring to FIG. 3, the counter circuits 140b and 140c are more concretely described below.

FIG. 3 is a diagram showing a more concrete structure example of the counter circuit 140. As shown in FIG. 3, the counter circuit 140 includes an initial stage counter circuit 310, a latch circuit 320, a register 330, and an operation circuit 340.

Initial Stage Counter Circuit 310

The initial stage counter circuit 310 is structured to count changes in the amplitude of the oscillation signal 121. More concretely, the initial stage counter circuit 310 continues continuously counting up count values by detecting at least one of rising edges or falling edges of the oscillation signal 121 that is an output signal of the oscillation circuit 120. By this, the number of pulses generated in the oscillation signal 121 is counted. It is noted that, when both of the rising edges and falling edges are detected and counted, a half of the counted values defines the number of pulses generated in the oscillation signal 121. Then, the initial stage counter circuit 310 outputs the counted value to the latch circuit 320.

Also, the initial stage counter circuit 310 may preferably be formed from a counter in which only one bit changes each time the count is updated. As an example of such a counter, a Johnson counter or a gray code counter may be enumerated, without any particular limitation to these counters.

Latch Circuit 320

The latch circuit 320 is structured to obtain a count value of the initial stage counter circuit 310 in synchronism with the gate clock signal 131. More specifically, the latch circuit 320 receives an asynchronous count value from the initial stage counter circuit 310 which is independent from the gate clock signal 131, and the latch circuit 320 latches the count value at rising edges or falling edges of the gate clock signal 131. In this manner, the latch circuit 320 counts pulses specified by rising edges or falling edges of the oscillation single 121 in each period of the gate clock signal 131. The latch circuit 320 outputs the latched count value to the register 330 and the operation circuit 340.

Register 330

The register 330 is structured to temporarily retain the count value inputted from the latch circuit 320, and output the retained count value to the operation circuit 340 in synchronism with edges of the gate clock signal 131 with which the latch circuit 320 latches the count value of the initial stage counter circuit 310. With this structure, a count value previously obtained and a count value newly obtained by the latch circuit 320 are inputted in the operation circuit 340.

Operation Circuit 340

The operation circuit 340 is structured to calculate a difference between the count value newly obtained and the count value previously obtained by the latch circuit 320, and output the difference as a count signal 141. More specifically, the operation circuit 340 subtracts the count value inputted from the register 330 from the count value inputted from the latch circuit 320, and outputs the difference as the count signal 141. In other words, the count value outputted from the operation circuit 340 indicates the number of pulses of the oscillation signal 121 generated during a period of the gate clock signal 131 from the previous rising edge or falling edge to the current rising edge or falling edge. It is noted that, in accordance with the present embodiment, the count signal 141 outputted from the operation circuit 340 may be composed of multiple bits, without any particular limitation to such a composition. Also, count values other than the count signal 141 indicated by a single signal line in the figure may be composed of multiple bits.

A structure example of the counter circuit 140 in accordance with the present embodiment is described above. It is noted that the count system for counting oscillation signals using the count circuit may be called a direct count method.

The initial stage counter circuit 310 can be composed with bits in a number that can express a value obtained by multiplying the amount of maximum change in the frequency of the corresponding crystal vibrator 110 that occurs when substance is adsorbed to the crystal vibrator with a reciprocal of the frequency of the gate clock signal 131. More specifically, when it is designed that an absolute value Δf of a frequency difference that can change when substance is adsorbed to the crystal vibrator 110 is 10 Hz, and the frequency of the gate clock signal 131 is 2 Hz, the initial stage counter circuit 310 may be composed with bits in a number that can express a value (10/2=)5, in other words, 3 bits. By this composition, the initial stage counter circuit 310 that does not have an unnecessarily large number of bits, but has a minimum requirement number of bits, can be composed.

Data Processing Circuit 150

The data processing circuit 150 is structured to specify substance contained in the medium surrounding the crystal vibrators 110a-110c based on the count signals 141b and 141c respectively outputted from the counter circuit 140b and 140c, and the data base 160 to be described below. Also, the processing circuit 150 obtains count signals 141b and 141c in synchronism with the gate clock signal 131. More specifically, for example, the data processing circuit 150 measures the count signals 141b and 141c as time variations in the frequencies of the crystal vibrators 110b and 110c, respectively. The data processing circuit 150 measures the amount of change, the rate of change, and the time constant of the frequency based on the time variation in the frequency, and performs pattern recognition processing with reference to the database 160. By this process, the data processing circuit 150 specifies substance included in the medium surrounding the crystal vibrators 110a-110c.

It is noted that the period in which the data processing circuit 150 acquires the count signal 141b and 141c may preferably be made longer, depending on the characteristic of the response speed of the sensor system in accordance with the present embodiment, within the range that does not lower the accuracy as the sensor. By this, the count signals 141b and 141c that are to be outputted from the counter circuits 140b and 140c, respectively, can be cropped and outputted. This makes it possible to reduce the load on the data processing circuit 150, reduce the power consumption, and reduce the circuit scale. Here, as the response speed of the sensor system is generally in seconds, the period in which the data processing circuit 150 acquires the count signal 141b and 141c may preferably be 0.1 seconds or greater. More preferably, the period may be 0.3 seconds or greater, whereby the load on data processing can be reduced without harming the accuracy in detecting substance included in the surrounding medium. In this case, the period in which the counter circuit 140 outputs the count signal 141b and 141c may also preferably be made longer with the acquisition period of the data processing, whereby the power consumption can be further reduced.

Database 160

The database 160 stores information indicative of the relation between changes in the count signals 141b and 141c and substances included in media surrounding the crystal vibrators 110a-110e, as information necessary for the data processing circuit 150 to identify the substance included in the medium. It is noted here that the information indicative of relations between changes in the count signals 141b and 141c and substances included in media may be, for example, information about the amount of change in the frequency, the rate of change and the time constant of frequency for correlating the change in each of the count signals 141b and 141c with the amount of substance adhered to the corresponding one of the crystal vibrators 110b and 110c.

(2) Operation of Sensor System

Next, a concrete example of operations of the sensor system is described with reference to FIGS. 1 to 3.

First, as the adsorption films are provided on the crystal vibrators 110b and 110c, the oscillation signals 121b and 121c outputted from the respective corresponding oscillation circuits 120b and 120c change, when substance contained in the surrounding medium adheres to the crystal vibrators 110b and 110c. In contrast, as no adsorption film is provided on the crystal vibrator 110a, the oscillation signal 121a outputted from the corresponding oscillation circuit 120a does not change due to substance contained in the surrounding medium.

The gate clock generation circuit 130 may use, for example, half-frequency dividers in 20 stages, thereby frequency-dividing the oscillation signal 121a two to the twentieth power ($2^{20}$) times (about one million times) to generate the gate clock signal 131, and output the same to the counter circuits 140b and 140c, and the data processing circuit 150.

Next, as shown in FIG. 3, the initial stage counter circuit 310 counts the number of occurrences of rising edges of the oscillation signal 121 by count-up. The latch circuit 320 acquires count values outputted from the initial stage counter circuit 310 at rising edges of the gate clock signal 131, and outputs the count value to the register 330 and the operation circuit 340.

At the timing the latch circuit 320 outputs the acquired count value, the register 330 retains the count value that has been previously attained (attained last time), and outputs the same to the operation circuit 340. The operation circuit 340 calculates a difference between the count value previously acquired by the latch circuit 320 and the count value newly acquired by the latch circuit 320, and outputs the result as a count signal 141.

Next, as shown in FIG. 1, the count signal 141b outputted from the counter circuit 140b, the count signal 141c outputted from the counter circuit 140c, and the gate clock signal 131 are inputted in the data processing circuit 150. The data processing circuit 150 can specify the substance adsorbed to the crystal vibrators 110b and 110c, based on these input signals, with reference to the database 160.

It is noted that, in this example, the gate clock signal 131 is generated by frequency-dividing the oscillation signal 121a two to the twentieth power ($2^{20}$) times, but it is not particularly limited thereto. In particular, for sensor systems using the direct count method like the present embodiment, it is empirically known that a gate clock signal 131 having a frequency around 1 Hz may preferably be used. By this, substance included in a target medium can be more accurately specified.

(3) Characteristics of Embodiment 1

The present embodiment may be characterized, in particular, by the gate clock signal 131 in the sensor system and the electric circuit 102 equipped with the counter circuits 140b and 140c.

The drift cancelling mechanism in accordance with the present embodiment will be described below, using an oscillation period (seconds) that is the reciprocal of a frequency (Hz=sec$^{-1}$), to facilitate the understanding of the mechanism. A frequency variation rate may simply be replaced with a frequency period variation rate. Let us assume that the periods of the oscillation signals 121a-121c corresponding to the entire channels of the crystal vibrators 110a-110c equally drift in an increasing direction by a variation rate of 1 ppm due to an environmental factor such as the temperature. As the period (gate time) of the gate clock signal 131 is defined by the predetermined frequency/time of the oscillation signal 121a corresponding to the crystal vibrator 110a that functions as a correction channel, the gate time also increases by 1 ppm when the oscillation period of the correction channel increases by 1 ppm. On the other hand, outputs from the counter circuits 140b and 140c corresponding to the crystal vibrators 110b and 110c that function as detection channels equal to frequencies during the gate time, in other words, values obtained by dividing the gate time by the respective oscillation periods. When the gate time and the oscillation period both change by 1 ppm, their ratio remains constant, and no change (drift) appears in the frequency that is the ratio between the two. In other words, the frequency of each of the detection channels in which drifts are always cancelled is outputted.

According to the electric circuit of the embodiment described above, changes in the surrounding environment such as the temperature surrounding the crystal vibrator 110a that functions as a first vibrator and the crystal vibrators 110b and 110c that function as second vibrators occur to generally the same degree, such that the frequencies of the oscillation signals 121a-121c increase or decrease at the same ratio. The counter circuits 140b and 140c perform counting, while using the relative relation between the oscillation signal 121a and the oscillation signal 121b or 121c which increase or decrease at the same ratio according to changes in the surrounding environment in the manner described above, thereby mutually cancelling the increase or the decrease in the frequencies of the oscillation signals. Accordingly, due to the relation between the oscillation signal 121a and the oscillation signal 121b or 121c, drifts would not affect the count signals 141b and 141c counted respectively by the counter circuits 140b and 140c, such that substance included in the surrounding medium can be properly detected regardless of changes in the surrounding environment. Further, without obtaining absolute values of the frequencies of the respective oscillation signals 121a-121c, it is possible to obtain the amounts of changes in the frequencies of the oscillation signals 121b and 121c necessary for detecting substance included in the surrounding medium. This makes it possible to structure a simple and small-sized electric circuit without using a highly accurate frequency measurement apparatus, an operation circuit for cancelling drifts, or the like.

Also, the crystal vibrators 110a-110c are provided on the same surface (on the same substrate in the present embodiment), whereby the crystal vibrators 110a-110c can be disposed spatially close to one another. By this, influence of temperature difference that may be caused if the crystal vibrators 110a-110c were spatially separated far from one another can be suppressed to a minimum.

Also, according to the electric circuit in accordance with the embodiment described above, the counter circuit 140 can count changes in the amplitude of the oscillation signal 121 without omission, whereby substance included in the surrounding medium can be more accurately detected.

Also, according to the electric circuit in accordance with the embodiment described above, the initial stage counter circuit 310 is structured such that only one bit in the count value changes at the time of count-up. In the latch circuit 320, when a count value is obtained while the count value of the initial stage counter circuit 310 is in transition from a value before count-up to a value after count-up, there may be a chance of acquiring a value before count-up at a certain bit in the count value, and a value after count-up at another bit. In this case, depending on the structure of the initial counter circuit 310, a series of count values obtained by the latch circuit 320 may be completely different from either of the values before and after count-up, whereby a so-called static hazard occurs. In this respect, according to the structure described above, a maximum error in the count value obtained is confined within the range of a LSB, such that the latch circuit 320 would hardly be affected even if the count value of the initial stage counter circuit 310 is obtained in transition from a value before count-up to a value after count-up. This makes it possible to avoid static hazards that can occur in the counter circuit 140.

Also, the counter circuit 140 in the electric circuit in accordance with the embodiment described above can output the count signal 141 at a period of a predetermined multiple of the period of the gate clock signal 131. According to such a structure, the count signal 141 to be outputted from the counter circuit 140 can be cropped and outputted, such that the power consumption of the electric circuit can be reduced. Also, it becomes possible to reduce the power consumption of the data processing circuit 150 for processing the count signal 141 that is connected to the electric circuit, and reduce the circuit scale smaller.

Moreover, a sensor system equipped with an electric circuit, the data processing circuit 150 and the database 160 is equipped with one of the electric circuits described above. Therefore, it is possible to form a sensor system equipped with a simple and small-sized electric circuit without using, for example, a frequency measurement apparatus with high accuracy.

3. Embodiment 2

Figure 4:
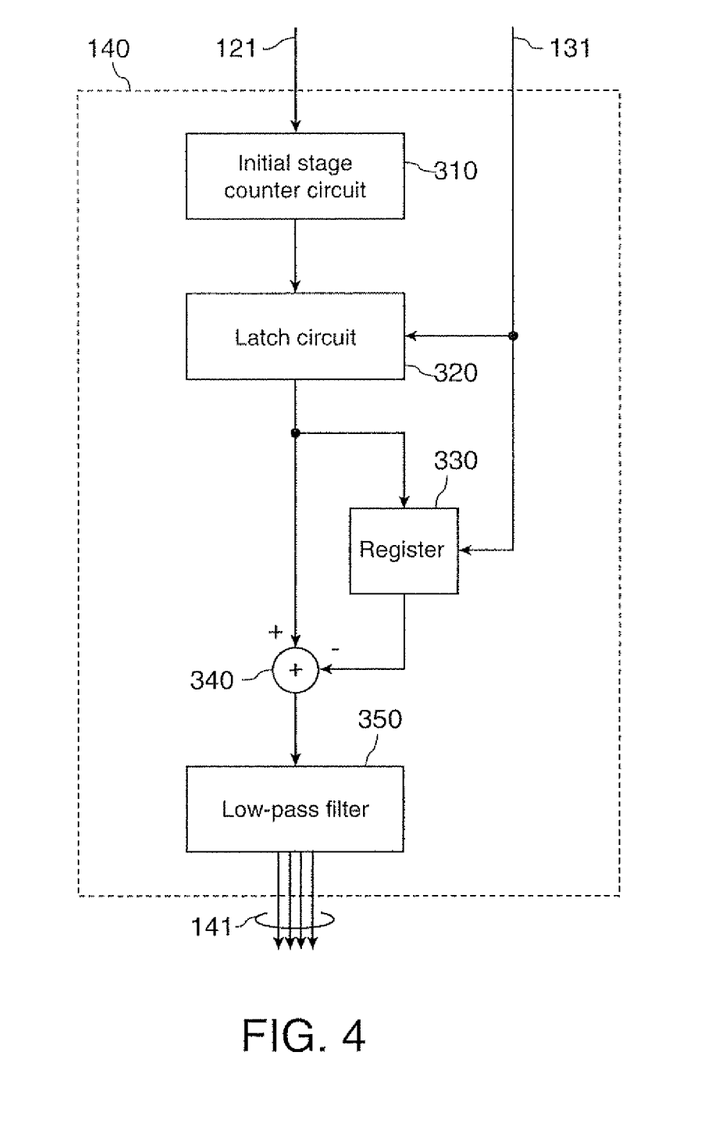
FIG. 4 is a diagram schematically showing a structure example of a counter circuit in accordance with Embodiment 2.

Next, a sensor system in accordance with a second embodiment is described in detail. In the present embodiment, the structure of the counter circuit 140 of Embodiment 1 is provided with a different composition, other parts of the structure are basically the same as those of Embodiment 1. However, while the direct count method is used in Embodiment 1, a short gate count method is used in the present embodiment, and therefore the gate clock generation circuit 130 operates in a different manner. Differences from Embodiment 1 are mainly described below, and compositions and operations similar to those of Embodiment 1 are omitted.

(1) Structure and Operation of Sensor System

FIG. 4 is a schematic diagram of a counter circuit 140 in accordance with the present embodiment. As shown in FIG. 4, the counter circuit 140 is structured with an initial stage counter circuit 310, a latch circuit 320, a register 330, an operation circuit 340, and a low-pass filter 350. As it is clear from comparing with the counter circuit 140 of Embodiment 1 shown in FIG. 3, the counter circuit 140 in accordance with the present embodiment is additionally provided with the low-pass filter 350.

Low-Pass Filter 350

The low-pass filter 350 removes high frequency components from a count signal outputted from the operation circuit 340, and outputs, from the counter circuit 140, a count signal 141 from which high frequency components are removed. The low-pass filter 350 can be formed from an analogue filter or a digital filter, or a combination thereof. When digital filter are used, finite impulse response (FIR) filters, infinite impulse response (IIR) filters, or moving average filters may be used. In particular, moving average filters are favorable as they have a simple structure, and their performance can be readily improved by serially connecting them in plurality. For example, the use of digital moving average filters in two stages with a cut-off frequency of 10 Hz is more preferable as sufficient performance can be obtained with a relatively simple structure.

Gate Clock Generation Circuit 130

The gate clock generation circuit 130 in accordance with the present embodiment generates a gate clock signal 131 having a higher frequency than that of Embodiment 1. For example, when the frequencies of the oscillation signals 121$b$ and 121$c$ are assumed to be analog signals, a signal having a frequency that is 100 or more times, more preferably 1000 or more times the sampling frequency in A/D conversion may be used as the gate clock signal 131. In other words, the gate clock signal 131 may preferably have a frequency that is 100 or more times the frequency of time variation components of frequency variations in the oscillation signals 121$b$ and 121$c$. For example, when the time variation component of the oscillation signal 121$b$ is about 1 Hz, the gate clock signal 131 in accordance with the present embodiment may preferably have a frequency at 100 Hz or higher.

According to a more concrete example, for example, the crystal vibrator 110$a$ with the oscillation signal 121$a$ at about 33 MHz may be used. The gate clock generation circuit 130 frequency-divides the oscillation signal 121$a$ two to the fifteenth power ($2^{15}$) times, using half-frequency dividing circuits in five stages, thereby generating the gate clock signal having a frequency at about 1 kHz. Then, the operation circuit 340 shown in FIG. 4 outputs discrete values with quantization errors of about 1 kHz as count signals. The count signals are filtered by the low-pass filter 350, whereby changes in the frequency of the oscillation signal 121 can be obtained at a high resolving power. This is the same principle as that of the noise shaping effect achieved by oversampling with so-called delta-sigma ($\Delta\Sigma$) modulation. According to this short gate count method, by using the gate clock signal 131 with a higher frequency, higher frequency resolving power and time-resolving power can be obtained, compared to the direct count method.

In general, the time variation component of the oscillation signal 121 is about 0.05 Hz or higher, such that, by using the gate clock signal 131 with a frequency at 100 Hz or higher, necessary frequency resolving power and time-resolving power can be obtained.

(2) Characteristics of Embodiment 2

According to the electric circuit with the structure in accordance with the embodiment described above, low frequency components included in the count signal 141 can be effectively extracted by the low-pass filter 350, whereby frequency variation information included in the oscillation signal 121 can be effectively obtained.

Also, the gate clock signal 131 in the electric circuit with the structure in accordance with the embodiment described above may preferably have a frequency that is 100 or more times the frequency of time variation components of at least one of the frequencies of the oscillation signals 121$b$ and 121$c$.

In order to properly sample time variation components of the frequency of the oscillation signal 121, a signal having a frequency that satisfies the sampling theorem, which is a signal having a frequency twice the time variation component of the frequency of the oscillation signal 121, may preferably be used as the gate clock signal 131. Furthermore, oversampling may be performed with a signal having a frequency several 100 or more times the aforementioned frequency as the gate clock signal 131, whereby the so-called noise shaping effect is more effectively utilized, and frequency variation information contained in the oscillation signal 121 can be obtained with higher resolving power and higher S/N ratio. According to the structure described above, the gate clock signal 131 has a frequency that is 100 or more times the frequency of a time variation component of the frequency of the oscillation signal 121, such that frequency variation information included in the oscillation signal 121 can be obtained with sufficiently high resolving power.

Moreover, the gate clock signal 131 used in the electric circuit with the structure in accordance with the embodiment described above may preferably have a frequency at 1 kHz or higher. As a result, frequency variation information included in the oscillation signal 121 can be obtained with sufficiently high resolving power.

In accordance with the present embodiment, when the frequency (Hz) of the gate clock signal is made higher than the amount of variation (Hz) in the frequency of the oscillation signals 121$b$ and 121$c$, the initial stage counter circuit 310 can be made of a 1-bit counter. In this case, the circuit scale of the initial stage counter circuit 310 can be reduced, and the power consumption can be reduced.

4. Embodiment 3

Figure 5:
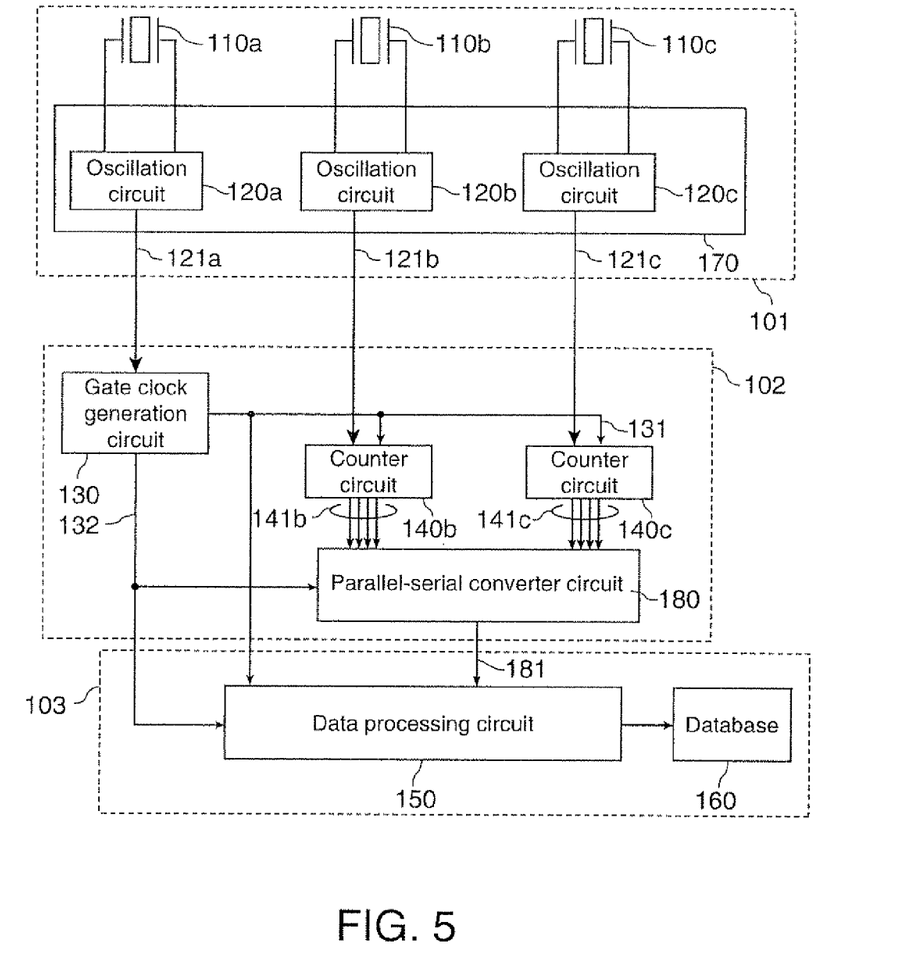
FIG. 5 is a diagram schematically showing a structure example of a sensor system in accordance with Embodiment 3.

Next, a sensor system in accordance with a third embodiment is described below. The present embodiment has a structure with a parallel-serial converter circuit 180 added to the structure of Embodiment 1, and other parts of the structure of Embodiment 3 are basically the same as those of Embodiment 1. Differences from Embodiment 1 are mainly described below, and compositions and operations similar to those of Embodiment 1 are omitted.

(1) Structure and Operation of Sensor System

FIG. 5 is a schematic diagram of a structure of a sensor system in accordance with the present embodiment. As shown in FIG. 5, the sensor system in accordance with the present embodiment is structured with crystal vibrators 110$a$-110$c$, oscillation circuits 120$a$-120$c$, a gate clock generation circuit 130, counter circuits 140$b$ and 140$c$, a data processing circuit 150, a database 160 and a parallel-serial converter circuit 180.

Parallel-Serial Converter Circuit 180

The parallel-serial converter circuit 180 is structured to sequentially convert count signals 141$b$ and 141$c$ that are parallel signals respectively outputted from the counter circuits 140$b$ and 140$c$ into serial signals 181 and output the same. For example, the parallel-serial converter circuit 180 may be structured with a parallel-input/serial-output shift register or the like. Also, a serialization clock 132 is inputted in the parallel-serial converter circuit 180 from the gate clock generation circuit 130, whereby the parallel signal is converted by the serialization clock 132 into the serial signal 181.

Gate Clock Generation Circuit 130

The gate clock generation circuit 130 generates, based on the oscillation signal 121a, a serialization clock 132 having a frequency higher than the gate clock signal 131, and outputs the serialization clock 132 to the parallel-serial converter circuit 180 and the data processing circuit 150.

Data Processing Circuit 150

The data processing circuit 150, first, decodes the serial signal 181 inputted from the parallel-serial converter circuit 180 into parallel signals based on the serialization clock 132. The decoded parallel signals are the same signals as the count signals 141b and 141c, such that the data processing circuit 150 can specify substance contained in the target medium in a similar manner as that of Embodiment 1.

(2) Characteristics of Embodiment 3

According to the sensor system with the structure of the embodiment described above, the number of wirings between the counter circuits 140b and 140c and the data processing circuit 150 can be substantially reduced, such that the sensor system with a simpler structure can be composed.

5. Supplementation

The embodiments have been described above with reference to examples using the crystal vibrators 110a-110c. However, instead of the crystal vibrators, other vibrators, such as, surface acoustic wave vibrators, bulk acoustic wave vibrators and ceramics vibrators may be used. All of the vibrators used in the sensor system may preferably have similar temperature characteristics, and more preferably have the same temperature characteristics.

Also, the embodiments have been described above with reference to examples using the direct count method or the short gate count method. However, for example, it is possible to use a reciprocal count method.

Furthermore, the embodiments have been described above with reference to examples using the Johnson counter or the gray code counter in order to avoid static hazards that can be generated at the counter circuit 140. However, it is also possible to use a method in which an ordinary counter is used, and the latch timing is adjusted.

It is noted that any one of the embodiments described is applicable to a sensor device equipped with an electric circuit, a plurality of vibrators and a plurality of oscillation circuits.

It is noted that the embodiments described above may be mutually combined. For example, Embodiment 2 and Embodiment 3 may be combined.

Also, in the embodiments described above, the crystal vibrators 110a-110c are provided on a common substrate. However, without any particular limitation to the above, it is sufficient if the crystal vibrators 110a-110c are disposed mutually close to one another. However, disposing the crystal vibrators 110a-110c on the same substrate is more preferable as they can be arranged close to one another.

What is claimed is:

1. A sensor system comprising:
an electric circuit including:
a reference signal generation circuit that generates a reference signal based on a first oscillation signal, the first oscillation signal being an oscillation signal of a first oscillation circuit that vibrates a first vibrator; and
a counter circuit that counts a second oscillation, the counter circuit counting the second oscillation signal based on the reference signal, the second oscillation signal being an oscillation signal of a second oscillation circuit that vibrates a second vibrator, the counter circuit outputs a count signal,
the count signal being based on a change of frequency of the second oscillation signal; wherein the counter circuit further includes an initial stage counter circuit that counts a pulse number of the second oscillation signal, a latch circuit that obtains a count value of the initial stage counter circuit synchronizing with the reference signal, and an operation circuit that calculates a difference between a first count value newly obtained by the latch circuit and a second count value previously obtained by the latch circuit, and outputs the difference as the count signal;
a database that is input relations between changes of the frequency of the second oscillation signal and a plurality of substances contained in a medium existing around the second vibrator; and
a data processing circuit that specifies one of the plurality of substances contained in the medium based on a serial signal output from the electric circuit and the database, wherein the count signal output from the counter circuit is a parallel signal, and further comprising a parallel-serial converter circuit that converts the count signal to the serial signal and outputs the serial signal.

2. The sensor system according to claim 1, wherein the reference signal generation circuit generates the reference signal having a frequency lower than a frequency of the first oscillation signal.

3. The sensor system according to claim 1, wherein the initial stage counter circuit is structured such that only one bit of the count value changes at the time of count-up.

4. The sensor system according to claim 1, wherein the counter circuit further includes a low-pass filter circuit that removes high frequency components of the count signal output from the operation circuit.

5. The sensor system according to claim 1, wherein the reference signal has a frequency that is 100 or more times a frequency of a time variation component of the frequency of the second oscillation signal.

6. The sensor system according to claim 1, wherein the reference signal has a frequency of 100 Hz or higher.

7. The sensor system according to claim 1, wherein the counter circuit outputs the count signal in a period of a predetermined multiple of the period of the reference signal.

8. The sensor system according to claim 1, wherein the first vibrator and the second vibrator are provided on a common substrate.

9. The sensor system according to claim 1, the first oscillation circuit including the first vibrator; and the second oscillation circuit including the second vibrator, wherein the first vibrator and the second vibrator are provided on a common substrate.

10. The sensor system according to claim 1, the count signal being a change of count value of the second oscillation signal.

11. The sensor system according to claim 1, further comprising: a second counter circuit that counts a third oscillation signal, the second counter circuit counting the third oscillation signal based on the reference signal, the third oscillation signal being an oscillation signal of a third oscillation circuit that vibrates a third vibrator, and the second counter circuit outputs a second count signal, the second count signal being based on a change of frequency of the third oscillation signal.

12. The sensor system according to claim 11, further comprising: a first absorber disposed on the second vibrator, and a second absorber disposed on the third vibrator; the first oscillation circuit including the first vibrator; and the second oscillation circuit including the second vibrator, wherein the first vibrator and the second vibrator are provided on a common substrate.

* * * * *